US012788867B2

(12) United States Patent
Pouget et al.

(10) Patent No.: US 12,788,867 B2
(45) Date of Patent: Nov. 10, 2026

(54) DEVICE AND SYSTEM FOR TRANSPORTING MEDICAL DEVICES

(71) Applicant: Becton Dickinson France, Le Pont-de-Claix (FR)

(72) Inventors: Gaelle Pouget, Grenoble (FR); Liliane Chassin De Kergommeaux, Grenoble (FR); Victor Vaz, Varces-Allieres-Et-Risset (FR)

(73) Assignee: Becton Dickinson France, Le Pont-de-Claix (FR)

( * ) Notice: Subject to any disclaimer, the term of this patent is extended or adjusted under 35 U.S.C. 154(b) by 154 days.

(21) Appl. No.: 18/833,066

(22) PCT Filed: Jan. 27, 2023

(86) PCT No.: PCT/EP2023/051966
§ 371 (c)(1),
(2) Date: Jul. 25, 2024

(87) PCT Pub. No.: WO2023/144285
PCT Pub. Date: Aug. 3, 2023

(65) Prior Publication Data

US 2025/0144288 A1 May 8, 2025

(30) Foreign Application Priority Data

Jan. 28, 2022 (EP) .................................... 22305103

(51) Int. Cl.
*A61M 5/00* (2006.01)

(52) U.S. Cl.
CPC .................................. *A61M 5/008* (2013.01)

(58) Field of Classification Search
CPC .............................. A61M 5/008; A61M 5/002
USPC ................................ 206/366, 365, 478, 557
See application file for complete search history.

(56) References Cited

U.S. PATENT DOCUMENTS 8,100,263 B2 * 1/2012 Vanderbush ............ B65B 31/06 206/524.8
8,915,363 B2 * 12/2014 Hawkes ............... A61C 19/002 206/370
2014/0308181 A1 * 10/2014 Blumentritt ........... B01L 3/0275 422/560

(Continued)

FOREIGN PATENT DOCUMENTS

WO WO-2021126676 A1 * 6/2021 ............ A61M 5/008

*Primary Examiner* — Rafael A Ortiz
(74) *Attorney, Agent, or Firm* — The Webb Law Firm

(57) ABSTRACT

A device for supporting a plurality of medical containers includes a plate having upper and lower surfaces and a sidewall defining a plate perimeter and extending between the upper and lower surface. The sidewall includes four edges intersecting at corners. A longitudinal axis of the plate extends perpendicular to the upper surface. The plate defines a plurality of openings extending through the plate from the upper to lower surface. Each opening is configured to retain a medical container therein. The plate is dimensioned to be disposed in a packaging such that a distance measured between opposing edges of the sidewall is less than a distance measured between opposing sidewalls of an interior surface of the packaging. The device further includes at least two positioning elements coupled at a first end thereof to the plate. Each positioning element has a second end detached from the plate.

19 Claims, 4 Drawing Sheets

(56) References Cited

U.S. PATENT DOCUMENTS

| | | | | |
|---|---|---|---|---|
| 2017/0183113 | A1* | 6/2017 | Deutschle | G01G 17/06 |
| 2018/0126066 | A1* | 5/2018 | Narvekar | A61J 1/1412 |
| 2021/0170092 | A1 | 6/2021 | Zhou et al. | |

* cited by examiner

DEVICE AND SYSTEM FOR TRANSPORTING MEDICAL DEVICES

CROSS-REFERENCE TO RELATED APPLICATIONS

This application is the United States national phase of International Patent Application No. PCT/EP2023/051966, filed Jan. 27, 2023, and claims priority to European Patent Application No. 22305103.8, filed Jan. 28, 2022, the disclosures of which are hereby incorporated by reference in their entireties.

BACKGROUND OF THE INVENTION

Field of the Invention

The present disclosure relates generally to a device, which is commonly referred to in the art as a nest, for transporting medical containers, such as syringes, and to a system including such device.

Description of Related Art

Medical containers, such as pre-fillable or prefilled syringes, may be transported from one site to another site. For instance, medical containers may be transported from a manufacturing site to a site at which the medical containers may be filled with a medicinal fluid. By way of further example, the medical containers may be manufactured and filled at the same site and subsequently transported to a storage site in a sterile packaging. During transportation, the medical containers may be supported by a holding device, which may be referred to as a nest. The holding device may be disposed within a packaging having an opening allowing for placement of the holding device therein and subsequently sealed by a sealing cover. The container may be referred to as a tub.

External dimensions of the holding devices being slightly smaller than inner dimension of the packaging for ease of the assembly, the holding device may be susceptible to moving relative to the packaging during transportation. As a result of such movement during long-distance transport, the holding device rubs against an inner surface of the packaging and may wear away material of the packaging or of the holding device so as to create particles of the packaging material and/or the holding device material. Because the packaging is sealed by the sealing cover, the particles remain inside the packaging throughout the remainder of transportation and storage. Such particles may be dispersed within the packaging and thus disposed within or on the medical containers stored inside the packaging. When the medical containers arrive at the destination, the medical containers are intended to be in a ready-to-use condition. By way of non-limiting example, when the medical containers are pre-fillable syringes, the syringes are intended to be in a clean and sterile condition upon arrival at the filling site so that the syringes may be filled with medicinal fluid. If the particles of the packaging material and/or of the holding device material are dispersed within or on the syringes, the syringes are not in a ready-to-use condition and must be cleaned prior to filling in order to avoid contamination of the medicinal fluid with which the medical containers will be filled. Accordingly, there is a need for a packaging solution that would inhibit or altogether prevent the creation of particles within the packaging.

SUMMARY OF THE INVENTION

An objective of the present disclosure is to provide a device for supporting a plurality of medical containers solving the above-mentioned drawbacks. The device comprises a plate having an upper surface, a lower surface, and a sidewall defining a perimeter of the plate and extending between the upper surface and the lower surface. The sidewall comprises four edges connected by corners. A longitudinal axis of the plate extends perpendicular to the upper surface. The plate defines a plurality of openings extending therethrough from the upper surface to the lower surface. Each opening is configured to retain a medical container therein. The plate is dimensioned to be disposed in a packaging for transporting a plurality of medical containers such that a distance measured between opposing edges of the sidewall is less than a distance measured between opposing sidewalls of an interior surface of the packaging. The device further comprises at least two positioning elements coupled at a first end thereof to the plate. Each of the positioning elements have a second end opposite the first end detached from the plate.

When the plate is disposed in the packaging, each positioning element forms an acute angle relative to the longitudinal axis of the plate and extends a lateral distance beyond the sidewall of the plate such that each of the positioning elements contacts the interior surface of the sidewall of the packaging when the plate is disposed therein.

Typically, the first of the at least two positioning elements is at least partly disposed on first edge of the four edges, the second of the at least two positioning elements is at least partly disposed on a second edge of the four edges, the first edge and second edge being adjacent to each other.

In one embodiment, the first of the at least two positioning elements is exclusively disposed on a first edge of the four edges, the second of the at least two positioning elements is exclusively disposed on a second edge of the four edges, and the first edge and second edge are adjacent to each other.

In another embodiment, the first of the at least two positioning elements is disposed at a first corner, the second of the at least two positioning elements is disposed at a second corner, and the first and second corners are diagonally opposite each other. In this embodiment, when a positioning element is disposed at a corner, it is disposed at the intersection of two adjacent edges, and thus it disposed partly on a first edge and partly on a second edge adjacent to the first edge.

Certain preferred but non-limiting features of the device described above are the following, taken individually or in combination:

- the positioning element is a rigid element configured to be displaced such that the acute angle of the positioning element is variable by 1° when the plate having the positioning elements thereon is disposed within the packaging and when the plate is exterior to the packaging;
- the positioning element is a flexible element configured to be displaced such that the acute angle of the positioning element is variable by 65° to 80° when the plate having the positioning elements thereon is disposed within the packaging and when the plate is exterior to the packaging;
- the positioning elements are formed integrally with the plate;
- at least one positioning element is coupled to each edge of the sidewall; and/or the device comprises four positioning elements, and one positioning element is coupled to each corner of the sidewall.

Another objective of the present disclosure is to provide a packaging system for receiving a plurality of medical containers comprising a packaging comprising a sidewall extending from a bottom wall, an interior surface of the sidewall being stepped so as to define a ledge. The packaging system also comprises the device comprising the plate having the at least two positioning elements as previously described disposed in the packaging. The lower surface of the plate is disposed on the ledge and the positioning elements are disposed on the interior surface of the sidewall.

Certain preferred but non-limiting features of the packaging system described above are the following, taken individually or in combination:

- a surface of the positioning element disposed on the interior surface of the sidewall has a curvature at corners that corresponds to a curvature of the interior surface of the plurality of sidewalls;
- a minority of a surface area of the surface of the positioning element is disposed against the interior surface of the sidewall;
- an axial dimension of each positioning element is less than or equal to a longitudinal dimension measured between the ledge and an uppermost surface of the packaging;
- the plate comprising the positioning elements engages the interior surface of the sidewalls of the packaging by interference fit; and/or
- the device further comprises a plurality of chimneys, each chimney extends circumferentially about an opening of the plurality of openings and extends axially over the upper surface of the plate, each chimney configured to retain a medical container therein.

BRIEF DESCRIPTION OF THE DRAWINGS

The illustrations presented herein are not meant to be actual views of any particular component, device, or system, but are merely idealized representations which are employed to describe embodiments of the present invention. Other features, goals, and advantages of the present invention will appear more clearly upon reading of the detailed description that follows and with references to drawings provided by way of non-limiting examples wherein.

DESCRIPTION OF THE INVENTION

As used herein, relational terms, such as "first," "second," "top," "bottom," "upper," "lower," "over," "under," "on," "interior," "exterior," and the like, are used for clarity and convenience in understanding the disclosure and accompanying drawings and do not connote or depend on any specific preference, orientation, or order, except where the context clearly indicates otherwise As used herein, the terms "axial," "axially," "longitudinal," and "longitudinally" generally mean and refer to a direction along or parallel to a longitudinal axis of an element(s) of the plate and packaging described herein.

As used herein, the terms "lateral" and "laterally" generally mean and refer to a direction perpendicular to the central, longitudinal axis of the element(s) of the plate and packaging described herein.

As used herein, the term "about" in reference to a given parameter is inclusive of the stated value and has the meaning dictated by the context (e.g., it includes the degree of error associated with measurement of the given parameter).

As used herein, the term "and/or" includes any and all combinations of one or more of the associated listed items.

As used herein, the term "configured" refers to a size, shape, material composition, material distribution, orientation, and arrangement of one or more of at least one structure and at least one apparatus facilitating operation of one or more of the structure and the apparatus in a pre-determined way.

Figure 1A:
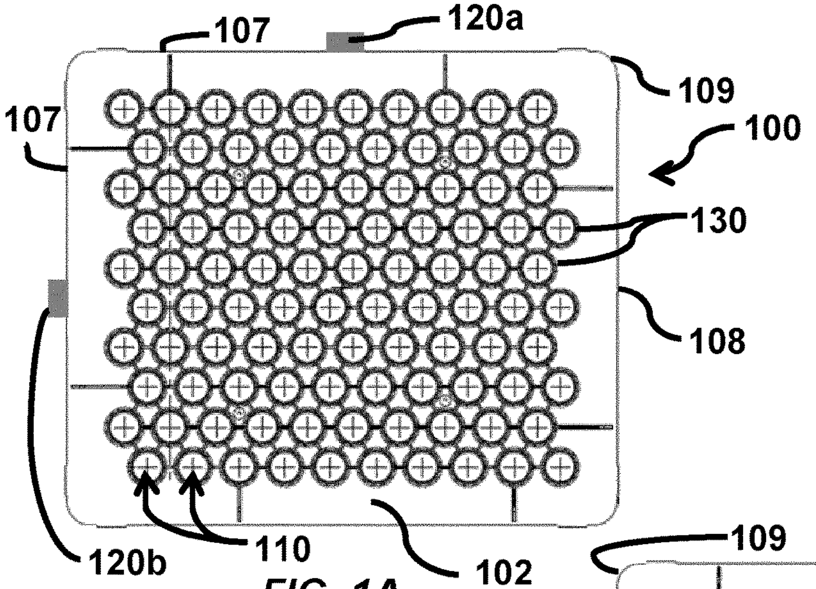
FIGS. 1A-1C are top, schematic views of a device for supporting a plurality of medical containers.
Figure 1B:
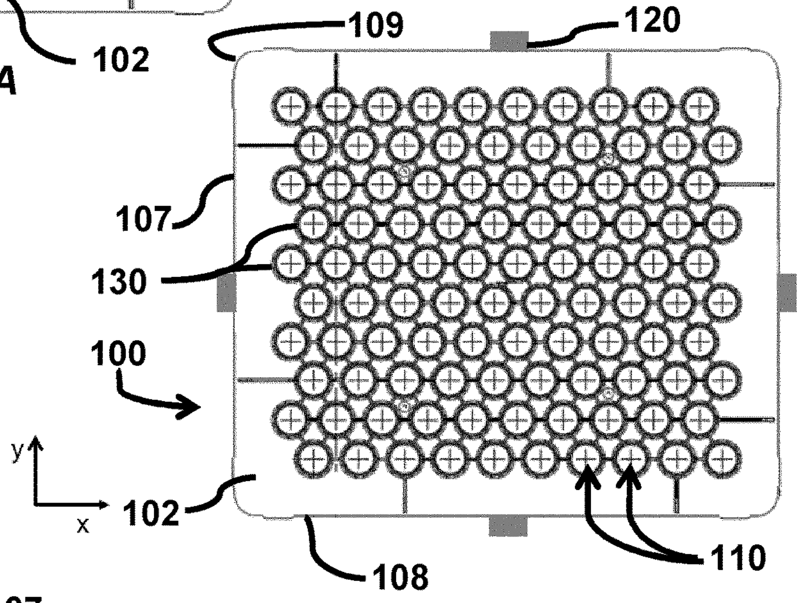
Figure 1C:
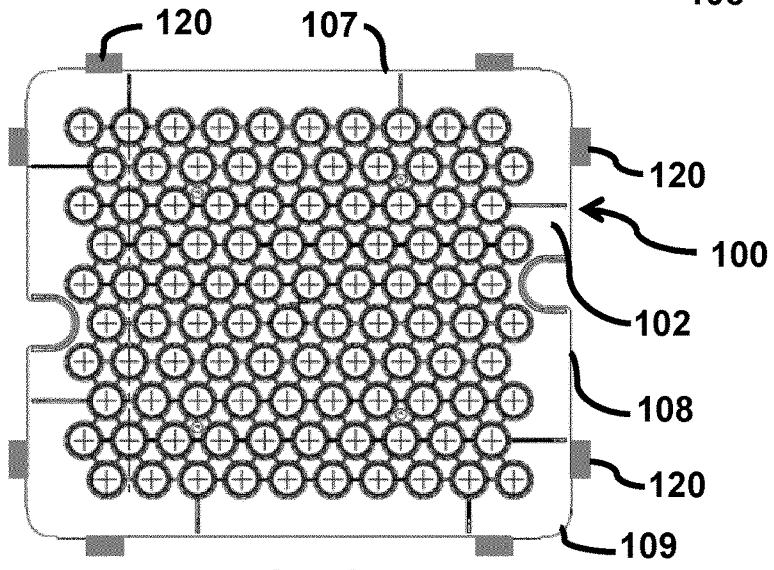

FIGS. 1A-1C illustrate a device 100 configured to support a plurality of medical containers therein. The device 100 may be referred to in the art generally as a nest. The medical containers may be vials, syringes, such as pre-fillable or prefilled syringes, or any medical element which may be transported in a nest, such as stoppers or syringe gaskets. The medical containers are configured, after filling, to contain a medical fluid therein.

The device 100 may comprise a plate 102 having an upper surface 104, a lower surface 106 (seen in FIG. 2), and a sidewall 108 extending between the upper surface 104 and the lower surface 106.

The sidewall 108 defines a perimeter of the plate 102. The sidewall 108 comprises four edges 107 connected by corners 109. The corners 109 may be rounded or pointed. The edges 107 may comprise planar surfaces. Such surfaces of opposing edges 107 may extend parallel to each other.

A longitudinal axis 101 of the plate 102 extends perpendicular to (e.g., normal to) the upper surface 104.

The plate 102 defines a plurality of openings 110 extending therethrough from the upper surface 104 to the lower surface 106. Each opening 110 is configured for a medical container to pass therethrough.

The plate 102 may also comprise a plurality of chimneys 130 that protrude axially from the upper surface 104. Each chimney 130 extends at least partially circumferentially about a corresponding opening 110. Each chimney 130 may be a generally cylindrical structure. Each chimney 130 defines an opening within which a medical container may be retained. Each chimney 130 may have a centrally extending longitudinal axis that is parallel with the longitudinal axis 101 of the plate 102. Each chimney 130 may be integrally formed with the plate 102.

The device 100 comprises at least two positioning elements 120. Each positioning element 120 extends between a first end 122 and a second end 124 opposite the first end 122. The first end 122 is coupled to the plate 102. The second end 124 is detached from the plate 102.

A first positioning element 120*a* is at least partly located (e.g., disposed) on a first edge 107. A second positioning element 120*b* is at least partly located on a second edge 107.

Typically, in a first embodiment, the first positioning element 120*a* may be exclusively (e.g., fully) located on a first edge 107. The second position element 120*b* may be exclusively located on a second edge 107 that is adjacent to the first edge 107. FIG. 1A illustrates an embodiment including two positioning elements 120 in such a configuration.

In further embodiments, the device 100 may include four positioning elements 120, as illustrated in FIG. 1B. One positioning element 120 may be positioned on each edge 107. In some embodiments, the positioning elements 120 may be distributed such that the positioning elements 120 on opposing edges 107 are disposed directly opposite each other. In other words, when the device 100 comprises four positioning elements 120, the position elements may be respectively located around the middle of each of the four edges 107 of the device 100 (e.g., intermediately between corners 109).

In yet further embodiments, the device 100 may include eight positioning elements 120, as illustrated in FIG. 1C. Two positioning elements 120 may be positioned on each edge 107. In some embodiments, the positioning elements 120 may be distributed such that one positioning element 120 on a given edge 107 is located directly opposite another positioning element 120 on a directly opposite edge 107.

In each of the foregoing embodiments, the positioning elements 120 may be positioned exclusively only edges 107 of the plate 102 such that the positioning elements 120 do not extend along the corners 109.

The location of the positioning elements 120 on at least two adjacent edges 107 as explained with references to FIGS. 1A-1C limits movement of the device 100 in two directions perpendicular to the longitudinal axis 101, including the x-direction and the y-direction as indicated by the coordinate system of FIG. 1B, when the device 100 is disposed within a packaging, or tub, and submitted to long-distance transport.

Figure 2:
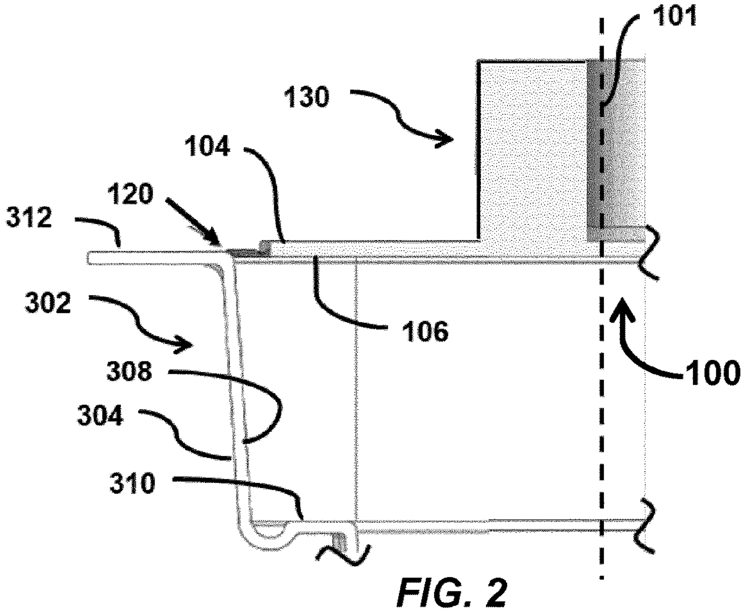
FIGS. 2-4 are partial, cross-sectional views of the device of FIGS. 1A-1C relative to a packaging.

The device 100 is dimensioned to be disposed in a packaging configured to transport a plurality of medical containers. FIG. 2 illustrates partial view of a packaging 302 in which the device 100 may be disposed. The device 100 and the packaging 302 collectively form a packaging assembly for transporting a plurality of medical containers.

The packaging 302 comprises a sidewall 304 defining a perimeter thereof and extending from a bottom wall 306. An interior of the packaging 302 is hollow and is defined by an interior surface of the bottom wall 306 and an interior surface 308 of the sidewall 304.

The sidewall 304 may be stepped so as to define a ledge 310. The ledge 310 provides a horizontal surface configured to support the device 100. When the device 100 is disposed in the packaging 302, the lower surface 106 of the device 100 is disposed on the ledge 310. The ledge 310 may extend continuously or discontinuously along a perimeter of the interior surface 308.

A flange may be provided at an end of the sidewall 304 opposite to which the bottom wall 306 is located. The flange defines an uppermost surface 312 of the sidewall 304. The flange may extend continuously about the perimeter of the sidewall 304.

The flange further defines a perimeter of an opening 314 through which the device 100 may be disposed within the packaging 302.

Figure 7:
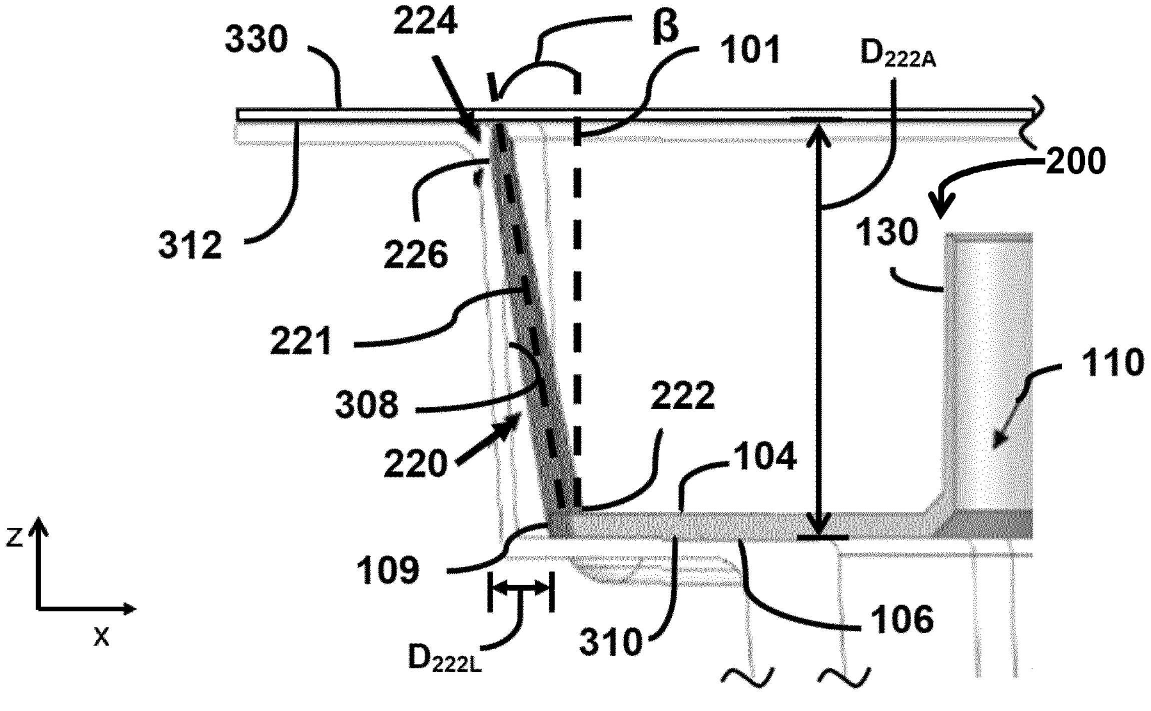
FIG. 7 is a partial, cross-sectional view of the device of FIGS. 5A-5B relative to a packaging.

At least a portion of the inner surface 308 of the sidewalls 304 may be sloped. More particularly, the inner surface 308 of the sidewall 304 extending between the ledge 310 and the uppermost surface 312 may be sloped. The slope of the sidewall 304 is best illustrated in FIGS. 2 and 7.

As previously stated, the device 100 is dimensioned to be disposed in the packaging 302 through the opening 314. More particularly, the plate 102 is dimensioned such that a distance measured between opposing edges 107 of the sidewall 108 (i.e., a lateral dimension being either a width or length of the plate 102 excluding the positioning element 120) is less than a distance measured between corresponding opposing interior surfaces 308 of the sidewall 304.

The positioning element 120 has an axis 121 extending between the first end 122 and the second end 124. The axis 121 of the positioning element 120 forms an angle α relative to the longitudinal axis 101 of the plate 102.

The positioning element 120 may be a flexible element. As used herein, the term "flexible element" refers to a positioning element 120 for which the angle α is movable by up to 90° relative to a first position when the device 100 is exterior to the packaging 302 and a second position when the device 200 is interior to the packaging 302. More particularly, the positioning element 120 is movable from the first position when the device 100 is exterior to the packaging 302 to a second position when the device is interior to the packaging 302 by 65° to 80°, inclusive.

Prior to disposing the device 100 within the packaging 302, the angle α of the positioning element 120 extends at 90° relative to the longitudinal axis 101, as illustrated in FIG. 2. As the device 100 is inserted through the opening 314 toward the ledge 310, the angle α decreases as an exterior surface 126 of the positioning element 120 engages with the interior surface 308 of the sidewall 304.

Figure 3:
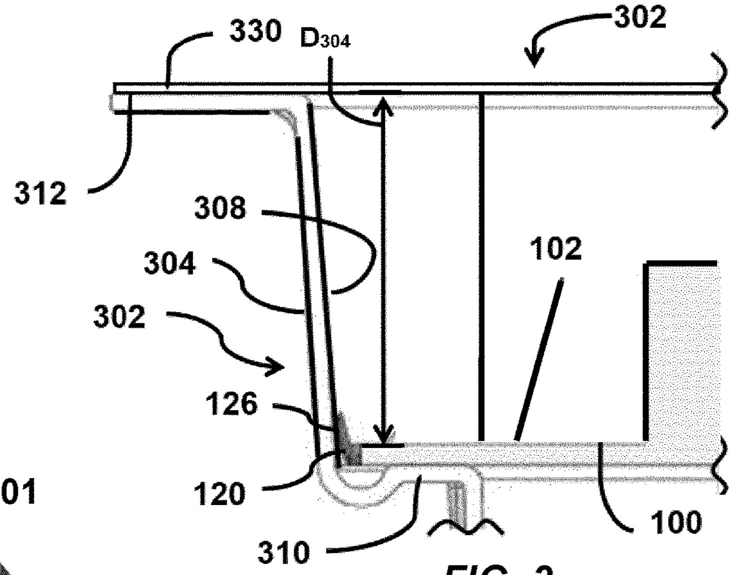
Figure 4:
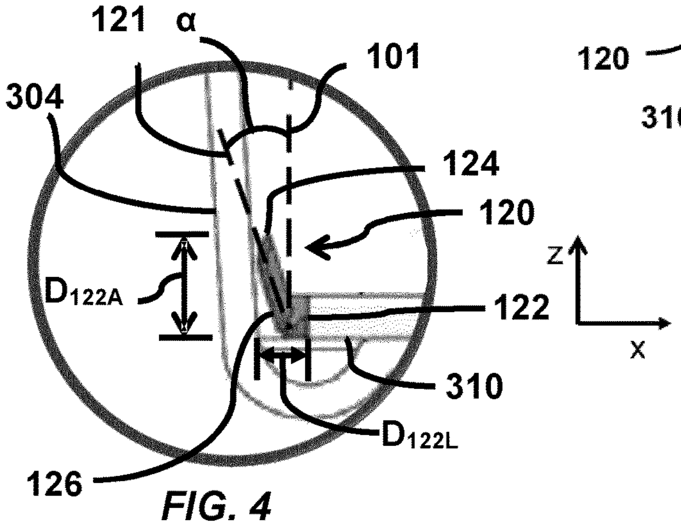

When the device 100 is disposed within the packaging 302 such that the lower surface 106 of the plate 102 is disposed on the horizontal surface of the ledge 310, as illustrated in FIGS. 3 and 4, the angle α of the positioning element 120 forms an acute angle relative to the longitudinal axis 101. The acute angle α may extending a range from 10° to 25°, inclusive, and, more preferably, in a range from 15° to 20°, inclusive.

The flexibility of the positioning elements 120 allows for the lateral dimensions of the device 100 to be reduced as the device 100 is disposed in the packaging 302. The flexibility of the positioning elements 120 also allows the device 100 to be removed from the packaging 302.

A given positioning element 120 projects axially (i.e., parallel to the longitudinal axis 101) beyond the upper surface 104 and laterally (i.e., perpendicular to the longitudinal axis 101) beyond the sidewall 108. Accordingly, each positioning element 120 has an axial dimension $D_{122A}$, which is measured as the positioning element 120 projects from the lower surface 106 to the second end 124 of the positioning element 120 and a lateral dimension $D_{122L}$, which is measured as the positioning element 120 projects from an edge 107 of the sidewall 108 at which the first end 122 of the positioning element 120 is coupled to the second end 124 of the positioning element 120.

Prior to disposing the device 100 within the packaging 302, the lateral dimension $D_{122L}$ of at least one positioning element 120 and the lateral dimension of the plate 102, when combined, are greater than the lateral dimension (i.e., distance measured between two opposing interior surfaces 308 of the sidewall 304 excluding the positioning elements 120) of the packaging 302.

When the device 100 is disposed in the packaging 302 and on the ledge 310, the device 100 and the packaging 302 are engaged by interference fit.

In some embodiments, such as the embodiment of FIG. 1A, when the device 100 is disposed within the packaging 302, a space may be located between the interior surface 308 of the sidewall 304 and at least two edges 107 and at least one corner 109 of the sidewall 108 of the plate 102. In other embodiments, such as the embodiments of FIGS. 1B and 1C, when the device 100 is disposed within the packaging 302, a space may be located between the interior surface 308 of the sidewall 304 and each edge 107 and corner 109 of the sidewall 108 of the plate 102. In such embodiments, there is no contact between the sidewall 304 and the sidewall 108.

When the device 100 is disposed within the packaging 302, a minority of a surface area of the exterior surface 126 of the positioning element 120 contacts the interior surface 308 of the sidewall 304.

The exterior surface 126 may be planar as the positioning element 120 extends along the edge 107. The planar exterior surface 126 corresponds to the planar surface of the sidewall 304 of the packaging 302 that the positioning element 120 contacts.

The engagement of the positioning elements 120 and, optionally, the sidewall 108 of plate 102 for embodiments lacking a positioning element 120 on each edge 107 with the inner surface 308 of the packaging 302 prevents the device 100 from moving in a direction perpendicular to the longitudinal axis 101 of the plate 102. As lateral movement between the device 100 and the packaging 302 is avoided, the device 100 and the packaging 302 do not rub inagainst each other so as to create particles of the packaging material and/or the device material.

The interference fit between the device 100 and the packaging 302 also prevents or limits movement of the device 100 along the Z direction through friction with the packaging 302. Preferably, both lateral and longitudinal movements between the device 100 and the packaging 302 are avoided.

Figure 5A:
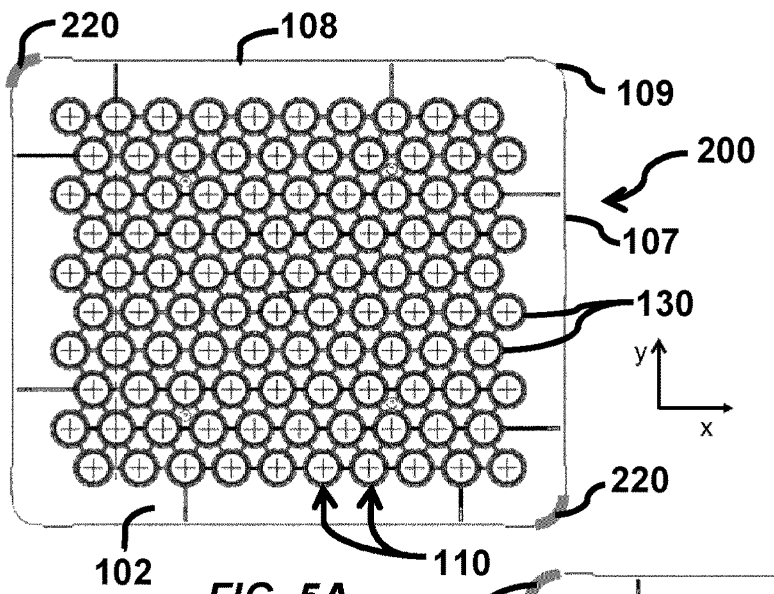
FIGS. 5A-5B are top, schematic views of another device for supporting a plurality of medical containers.
Figure 5B:
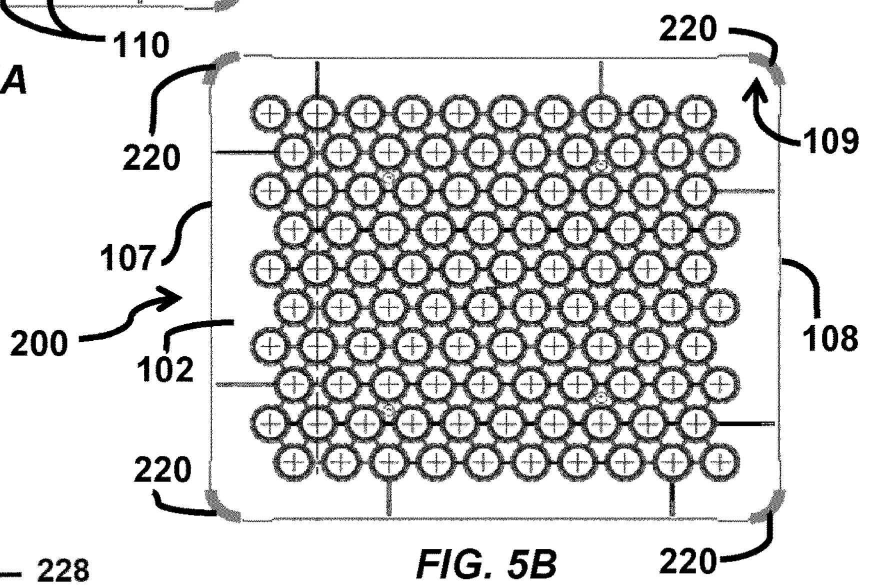

FIGS. 5A and 5B illustrate a device 200 configured to support a plurality of medical containers therein.

The device 200 comprises the plate 102 having the upper surface 104, the lower surface 106, and the sidewall 108 extending between the upper surface 104 and the lower surface 106, as previously described herein.

Figure 6:
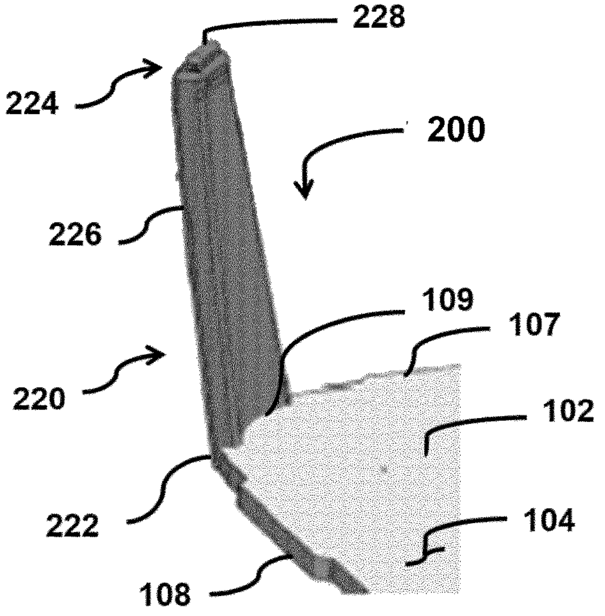
FIG. 6 is a partial, perspective view of the device of FIGS. 5A-5B.

The device 200 comprises at least two positioning elements 220. As illustrated in FIG. 6, each positioning element 220 may extend between a first end 222 and a second end 224 opposite the first end 222. The first end 222 is coupled to the plate 102. The second end 224 is detached from the plate 102.

A first positioning element 220*a* may be located at a first corner 109. A second position element 220*b* may be located at a second corner 109 that is diagonally opposite to the first corner 109. FIG. 5A illustrates an embodiment including two positioning elements 220. When a positioning element 220 is positioned at a corner 109 of the device 200, the positioning element is partly disposed on two adjacent edges 107.

In further embodiments, the device 200 may include four positioning elements 220, as illustrated in FIG. 5B. One positioning element 220 may be positioned at each corner 109.

The location of the at least two positioning elements 220 on diagonally opposed corners 109 limits movement of the device 200 in directions perpendicular to the longitudinal axis 101, including the x-direction and the y-direction as indicated by the coordinate system of FIG. 5A, when the device 200 is disposed within the packaging 302.

Each positioning element 220 has an axis 221 extending between the first end 222 and the second end 224. The axis 221 of the positioning element 220 forms an angle β relative to the longitudinal axis 101 of the plate 102.

The positioning element 220 may be a rigid element. As used herein, the term "rigid element" refers to a positioning element 220 for which the angle β is movable by up to 5° and, more particularly, by 1° between a first position when the device 200 is exterior to the packaging 302 and a second position when the device 200 is interior to the packaging 302.

Prior to disposing the device 200 within the packaging 302, the angle β of the positioning element 220 is about 5° greater than an angle of the sloped sidewall 304 of the interior surface 308 of the packaging 302 (e.g., an angle measured between a line tangent to the interior surface 308 of the sidewall 304 and the longitudinal axis 101). In some embodiments, the angle β of the positioning element 220 extends in a range from 31° to 46°, inclusive, and, more preferably, in a range from 36° to 41°, inclusive, relative to the longitudinal axis 101. As the device 200 is inserted through the opening 314 and toward the ledge 110, the angle β decreases as an exterior surface 226 of the positioning element 220 engages with the interior surface 308 of the sidewall 304.

When the device 200 is disposed within the packaging 302 such that the lower surface 106 of the plate 102 is disposed on the horizontal surface of the ledge 310, the angle β of the positioning element 220 forms an acute angle relative to the longitudinal axis 101. This acute angle β is about 4° larger than the angle between the interior surface 308 of the sidewall 304 and the longitudinal axis 101. Accordingly, the acute angle β may extend a range from 30° to 45°, inclusive, and, more preferably, in a range from 35° to 40°, inclusive, relative to the longitudinal axis 101, as illustrated in FIG. 7.

The flexibility of the positioning elements 220 allows the lateral dimensions of the device 100 to be reduced as the device 200 is disposed in the packaging 302. The flexibility of the positioning elements 220 also allows the device 200 to be removed from the packaging 302.

As discussed with reference to the device 100, the plate 102 is dimensioned such that a distance measured between opposing edges 107 of the sidewall 108 (i.e., a lateral dimension being either a width or length of the plate 102 excluding the positioning elements 220) is less than a distance measured between corresponding opposing interior surfaces 308 of the sidewall 304. The plate 102 is also dimensioned such that a distance measured between opposing corners 109 of the sidewall 108 (i.e., a lateral dimension being a diagonal of the plate 102) is less than a distance measured between diagonally opposing corners 316 of the packaging 302.

A given positioning element 220 projects axially beyond the upper surface 104. The positioning element 220 projects laterally beyond the sidewall 108 and, more particularly, laterally beyond the corner 109. The positioning element 220 has an axial dimension $D_{222A}$, which is measured as the position element 220 projects between the lower surface 106 and the second end 224 of the positioning element 220 and a lateral dimension $D_{222L}$, which is measured as the positioning elements 220 projects between a corner 109 of the sidewall 108 to which the first end 222 of the positioning element 220 is coupled and the second end 224 of the positioning element 220.

The axial dimension $D_{222A}$ is less than or equal to an axial dimension $D_{304}$ measured between the horizontal surface of the ledge 310 and the uppermost surface 312 of the sidewall 304. The longitudinal dimension $D_{304}$ is measured in a direction normal to the interior surface of the bottom wall 306.

When the axial dimension $D_{222A}$ is equal to the axial dimension $D_{304}$, the second end 224 of the positioning element 220 is disposed against (e.g., in contact with) a sealing element 330 as discussed in further detail below. The engagement of the positioning elements 220 and the sealing element 330 prevents the device 200 from moving in a direction parallel to the longitudinal axis 101 of the plate 102. As axial movement between the device 200 and the packaging 302 is avoided, the device 200 and the packaging 302 do not rub against each other so as to create particles of the packaging material and/or the device material.

The lateral dimension $D_{222L}$ of the positioning elements 220 and the diagonal dimension of the plate 102, when added, are greater than the lateral dimension (i.e., distance measured between two opposing corners 316 of the interior surface 308 of the sidewall 304) of the packaging 302.

When the device 200 is disposed in the packaging 302 and on the ledge 310, the device 200 and the packaging 302 are engaged by interference fit.

Figure 8:
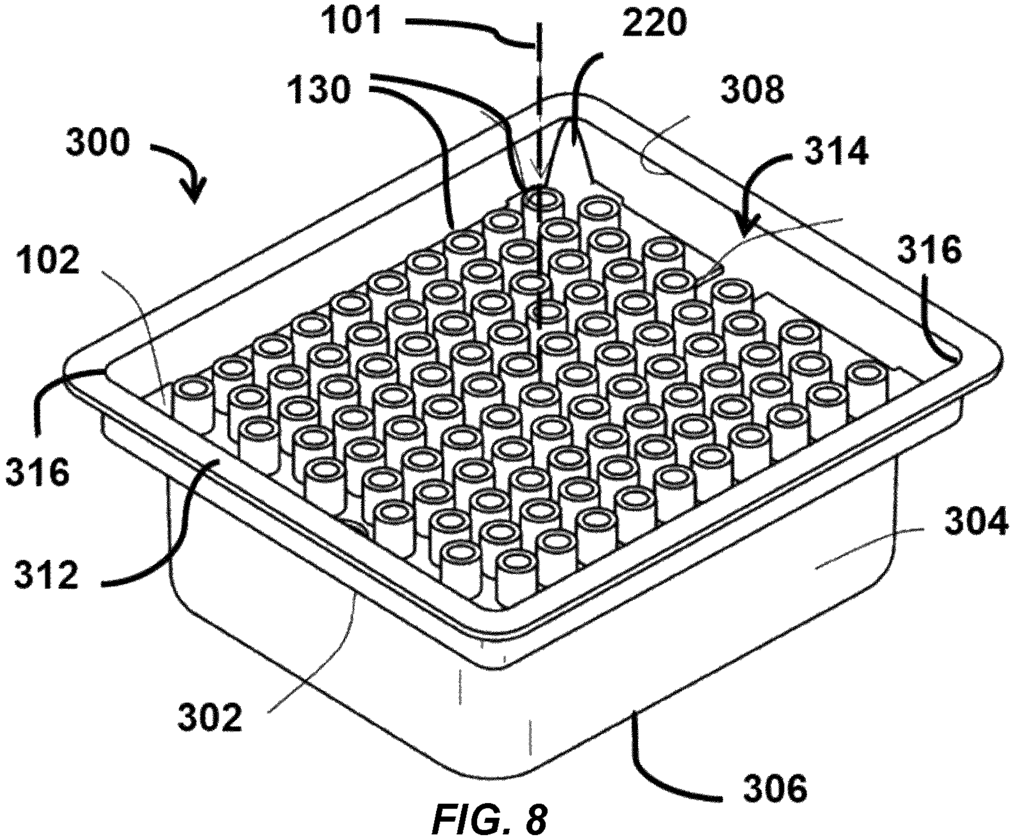
FIG. 8 is a perspective view of the device of FIGS. 5A-5B disposed in a packaging.

The device 200 and the packaging 302 collectively form a packaging assembly 300, as shown in FIG. 8, for transporting a plurality of medical containers.

When the device 200 lacking positioning elements according to the invention is disposed within the packaging 302, a space may be located between the interior surface 308 of the sidewall 304 and each edge 107 and corner 109 of the sidewall 108 of the plate 102. In such embodiments, there is insufficient contact between the sidewall 304 and the sidewall 108 and the device 200 can move in the packaging 302.

When the device 200 having the positioning elements 220 thereon is disposed within the packaging 302, the positioning element 220 may abut on the interior surface 308 of the sidewall 304. More particularly, an exterior surface 226 of each positioning element 220 may abut against the interior surface 308 of the sidewall 304.

A minority of a surface area of the exterior surface 226 is disposed against the interior surface 308 of the sidewall 304.

The exterior surface 226 may be curved as the positioning element 220 extends around the corner 109. A radius of curvature of the exterior surface 226 of the positioning elements 220 may be substantially equal to a radius of curvature of corners 316 of the sidewall 304 of the packaging 302. The curvature of the positioning elements 220 is visible in the top views of FIGS. 5A and 5B.

The engagement of the positioning elements 220 and the packaging 302 prevents the device 200 from moving in a direction perpendicular to the longitudinal axis 101 of the plate 102. As lateral movement between the device 200 and the packaging 302 is avoided, the device 200 and the packaging 302 do not rub against each other so as to create particles of the packaging material and/or the device material.

A sealing element 330 (FIGS. 3 and 7) may be coupled to the uppermost surface 306. The sealing element 330 is configured to close the opening 314 of the packaging 302 after the device 100, 200 is disposed therein and allow for sterilization of the packaging 302. The sealing element 330 is a microbial barrier. The sealing element 330 may be a porous microbial barrier. The sealing element 330 may also be permeable to a sterilization gas such that the interior of the packaging 302 can be sterilized after the sealing element 330 is disposed on the uppermost surface 306. The sterilization gas may be, for example, ethylene oxide. In an exemplary embodiment, the sealing element 330 may be formed of a TYVEK® sheet.

In some embodiments, the second end 224 of the positioning element 220 has a rounded surface 228. The rounded surface 228 is configured to contact the sealing element 330 without piercing the sealing element 330 during transportation of the assembly 300.

In any of the foregoing embodiments, the positioning elements 120, 220 may be formed integrally with the plate 102. In such embodiments, the positioning elements 120, 220 and the plate 102 are formed together in a one-shot or two-shot injection molding process. Alternatively, the positioning elements 120 may be separately formed from the plate 102 and coupled thereto by adhesive or other coupling means. The positioning elements 120, 220 may be formed from the same or different polymeric material as the plate 102.

While the present disclosure has been described herein with respect to certain illustrated embodiments, those of ordinary skill in the art will recognize and appreciate that it is not so limited. Rather, many additions, deletions, and modifications to the illustrated embodiments may be made without departing from the scope of the disclosure, including legal equivalents thereof. In addition, features from one embodiment may be combined with features of another embodiment while still being encompassed within the scope of the invention as contemplated by the inventors.

The invention claimed is:

1. A device for supporting a plurality of medical containers comprising:

a plate having an upper surface, a lower surface, and a sidewall defining a perimeter of the plate and extending between the upper surface and the lower surface, the sidewall comprising four edges intersecting at corners, a longitudinal axis of the plate extending perpendicular to the upper surface, the plate defining a plurality of openings extending through the plate from the upper surface to the lower surface, each opening configured to retain a medical container therein, the plate being dimensioned to be disposed in a packaging for transporting a plurality of medical containers such that a distance measured between opposing edges of the sidewall is less than a distance measured between opposing sidewalls of an interior surface of the packaging; and at least two positioning elements coupled at a first end thereof to the plate, each of the positioning elements having a second end opposite the first end detached from the plate, the first of the at least two positioning elements is at least partly disposed on a first edge of the four edges, the second of the at least two positioning elements is at least partly disposed on a second edge of the four edges, the first edge and second edge being adjacent to each other, wherein, when the plate is disposed in the packaging, each positioning element extends a lateral distance beyond the sidewall of the plate and axially beyond the upper surface of the plate such that each positioning element forms an acute angle relative to the longitudinal axis of the plate and such that each of the positioning elements contacts the interior surface of the sidewall of the packaging when the plate is disposed therein, and wherein each of the second end of each of the at least two positioning elements is located vertically above the upper surface of the plate along an axis of the acute angle extending between each of the first end and the second end of each of the at least two positioning elements.

2. The device of claim 1, wherein the first of the at least two positioning elements is disposed at a first corner, the second of the at least two positioning elements is disposed at a second corner, the first and second corners being diagonally opposite each other.

3. The device of claim 2, wherein each of the at least two positioning elements is a rigid element configured to be displaced such that the acute angle of the positioning element is variable by about 1° when the plate having the positioning elements thereon is disposed within the packaging and when the plate is exterior to the packaging.

4. The device of claim 2, wherein the device comprises four positioning elements, and one positioning element is coupled to each corner of the sidewall.

5. The device of claim 1, wherein the first of the at least two positioning elements is disposed exclusively on a first edge of the four edges, the second of the at least two positioning elements is disposed on a second edge of the four edges, the first edge and second edge being adjacent to each other, and the first positioning element being separate from the second position element.

6. The device of claim 5, wherein the positioning element is a flexible element configured to be displaced such that the acute angle of the positioning element is variable by 65° to 80° when the plate having the positioning elements thereon is disposed within the packaging and when the plate is exterior to the packaging.

7. The device of claim 5, wherein at least one positioning element is coupled to each edge of the sidewall.

8. The device of claim 1, wherein the positioning elements are formed integrally with the plate.

9. A packaging system for receiving a plurality of medical containers comprising:

a packaging comprising a sidewall extending from a bottom wall, an interior surface of the sidewall being stepped so as to define a ledge; and the device of claim 1 comprising the plate having the at least two positioning elements disposed in the packaging, wherein the lower surface of the plate is disposed on the ledge and wherein the positioning elements are disposed on the interior surface of the sidewall.

10. The packaging system of claim 9, wherein a surface of each of the at least two positioning elements disposed on the interior surface of the sidewall has a curvature at corners that corresponds to a curvature of the interior surface of the plurality of sidewalls.

11. The packaging system of claim 9, wherein a minority of a surface area of the surface of the positioning element is disposed against the interior surface of the sidewall.

12. The packaging system of claim 9, wherein an axial dimension of each positioning element is less than or equal to an axial dimension measured between the ledge and an uppermost surface of the packaging.

13. The packaging system of claim 9, wherein the plate comprising the positioning elements engages the interior surface of the sidewalls of the packaging by interference fit.

14. The packaging system of claim 9, wherein the device further comprises a plurality of chimneys, each chimney extends circumferentially about an opening of the plurality of openings and extends axially over the upper surface of the plate, each chimney configured to retain a medical container therein.

15. The device of claim 1, wherein each of the at least two positioning elements has an axial dimension $D_{122A}$, which is measured as each of the at least two positioning elements each projects from the lower surface to the second end of each of the at least two positioning elements, and a lateral dimension $D_{122L}$, which is measured as each of the at least two positioning elements projects from an edge of the sidewall at which the first end of each of the at least two positioning elements is coupled to the second end of each of the at least two positioning elements.

16. The device of claim 15, wherein, prior to disposing the device within the packaging, the lateral dimension $D_{122L}$ of each of the at least two positioning elements and a lateral dimension of the plate, when combined, are greater than a lateral dimension that is defined as a distance as measured between two opposing interior surfaces of the sidewall of the packaging excluding the at least two positioning elements.

17. The device of claim 1, wherein each of the at least two positioning elements has an axial dimension $D_{222A}$, which is measured as each of the at least two positioning elements each projects between the lower surface and the second end of each of the at least two positioning elements, and a lateral dimension $D_{222L}$, which is measured as each of the at least two positioning elements each projects between a corner of the sidewall to which the first end of each of the at least two positioning elements is coupled and the second end of each of the at least two the positioning elements.

18. The device of claim 17, wherein the axial dimension $D_{222A}$ is less than or equal to an axial dimension $D_{304}$ measured between the horizontal surface of a ledge of the sidewall and an uppermost surface of the sidewall of the packaging.

19. The device of claim 17, wherein the lateral dimension $D_{222L}$ of each of the at least two positioning elements and a diagonal dimension of the plate, when added, are greater than a lateral dimension that is a distance as measured between two opposing corners of the interior surface of the sidewall of the packaging.

* * * * *